(12) United States Patent
Clarke et al.

(10) Patent No.: US 8,642,654 B2
(45) Date of Patent: *Feb. 4, 2014

(54) HYDROXYBUTYRATE ESTER AND MEDICAL USE THEREOF

(75) Inventors: Kieran Clarke, Oxford (GB); Richard Lewis Veech, Rockville, MD (US)

(73) Assignees: ISIS Innovation Limited, Summertown (GB); Government of the USA, as Represented by the Sec-Retary, Department of Health and Human Services, Rockville, MD (US)

( * ) Notice: Subject to any disclaimer, the term of this patent is extended or adjusted under 35 U.S.C. 154(b) by 138 days.

This patent is subject to a terminal disclaimer.

(21) Appl. No.: 13/031,006

(22) Filed: Feb. 18, 2011

(65) Prior Publication Data

US 2011/0237666 A1 Sep. 29, 2011

(51) Int. Cl.
*A01N 37/02* (2006.01)
*A61K 31/22* (2006.01)
*C07C 69/66* (2006.01)

(52) U.S. Cl.
USPC .......................................... 514/546; 560/179

(58) Field of Classification Search
USPC .......................................... 514/546; 560/179
See application file for complete search history.

(56) References Cited

U.S. PATENT DOCUMENTS

| | | | |
|---|---|---|---|
| 5,112,865 A * | 5/1992 | Nichels et al. | 514/546 |
| 6,136,862 A * | 10/2000 | Hiraide et al. | 514/578 |
| 6,380,244 B2 | 4/2002 | Martin et al. | |
| 8,101,653 B2 | 1/2012 | Veech et al. | |

FOREIGN PATENT DOCUMENTS

| | | |
|---|---|---|
| JP | 54138126 | 10/1979 |
| WO | WO9841200 | 9/1998 |
| WO | WO2004108740 A2 | 12/2004 |

OTHER PUBLICATIONS

Shaw J H et al: "Influence of beta-hydroxybutyrate infusion on glucose and free fatty acid metabolism in dogs." Dec. 1984, The American Journal of Physiology Dec. 1984, vol. 247, Nr. 6 Pt 1, pp. E756-E764.
International Search Report and Written Opinion from PCT/US2009/040766 dated Aug. 6, 2009.
Desrochers et al., Metabolism of R and S-1,3-butanediol in perfused livers from meal-fed and starved rats, Biochem. J. (1992) 285, pp. 647-653.
Desrochers et al., Metabolism of (R,S)-1,3-butanediol acetoacetate esters, potential parenteral and enteral nutrients in conscious pigs, Am. J. Physiol. (1995) 268, pp. E660-E667.
Puchowicz et al., Dog model of therapeutic ketosis induced by oral administration of R,S-1,3-butanediol diacetoacetate, J Nutr. Biochem. (2000) 11, pp. 281-287.

* cited by examiner

*Primary Examiner* — Samira Jean-Louis
(74) *Attorney, Agent, or Firm* — Lathrop & Gage LLP; Brian C. Trinque; Andrew T. Wilkins

(57) ABSTRACT

A compound which is 3-hydroxybutyl 3-hydroxybutyrate enantiomerically enriched with respect to (3R)-hydroxybutyl (3R)-hydroxybutyrate of formula (I) is an effective and palatable precursor to the ketone body (3R)-hydroxybutyrate and may therefore be used to treat a condition which is caused by, exacerbated by or associated with elevated plasma levels of free fatty acids in a human or animal subject, for instance a condition where weight loss or weight gain is implicated, or to promote alertness or improve cognitive function, or to treat, prevent or reduce the effects of neurodegeneration, free radical toxicity, hypoxic conditions or hyperglycaemia.

5 Claims, 9 Drawing Sheets

HYDROXYBUTYRATE ESTER AND MEDICAL USE THEREOF

STATEMENT AS TO FEDERALLY SPONSORED RESEARCH

This invention was made with government support under Grant No. W911NF-05-1-0479 awarded by ARMY/ARO. The government has certain rights in this invention.

RELATED APPLICATIONS

This application is a 35 U.S.C. §111(a) filing of International Application Number PCT/US2009/040766 which was filed on Apr. 16, 2009, which claims priority to U.S. Provisional Application 61/090,751, which was filed on Aug. 21, 2008. The entire contents of the aforementioned applications are hereby incorporated herein by reference.

FIELD OF THE INVENTION

The present invention relates to hydroxybutyrate esters which elevate blood levels of ketone bodies, and to medical uses of such esters.

BACKGROUND TO THE INVENTION

Ketone bodies are chemical compounds which are produced by the liver from fatty acids released from adipose tissue. Ketone bodies themselves can be used as a source of energy in most tissues of the body. The intake of compounds that boost the levels of ketone bodies in the blood can lead to various clinical benefits, including an enhancement of physical and cognitive performance and the treatment of cardiovascular conditions, diabetes, neurodegenerative diseases and epilepsy.

Ketone bodies include (R)-3-hydroxybutyrate and acetoacetate. As discussed in WO2004/108740, these compounds could in theory be administered directly to achieve elevated levels of ketone bodies in a subject. However, direct administration of the compounds is unpractical and potentially dangerous. For example, direct administration of either (R)-3-hydroxybutyrate or acetoacetate in its free acid form can result in significant acidosis following rapid absorption from the gastrointestinal tract. Administration of the sodium salt of these compounds in unregulated amounts is also unsuitable due to a potentially dangerous sodium overload that could accompany administration of therapeutically relevant amounts of the compounds.

Against this background WO2004/108740 discloses derivatives of (R)-3-hydroxybutyrate which serve as precursors to ketone bodies such as acetoacetate and (R)-3-hydroxybutyrate and which therefore elevate blood concentrations of ketone bodies when administered to a subject. Examples of the derivatives include esters, for instance esters derived from a variety of alcohols. WO2004/108740 further discloses the use of these derivatives for treating metabolic disorders such as insulin deficiency and insulin resistance, and as nutritional supplements for increasing physical performance.

WO04/105742 teaches that compounds which reduce the level of free fatty acids circulating in the plasma of a subject may be used to treat muscle impairment or fatigue. Ketone bodies, such as ketone body esters, are given examples of such compounds.

SUMMARY OF THE INVENTION

It has now been surprisingly found that one particular enantiomer of one particular ester of 3-hydroxybutyrate is an effective and palatable precursor to the ketone body (3R)-hydroxybutyrate. Accordingly, the present invention provides a compound which is 3-hydroxybutyl 3-hydroxybutyrate enantiomerically enriched with respect to (3R)-hydroxybutyl (3R)-hydroxybutyrate of formula (I):

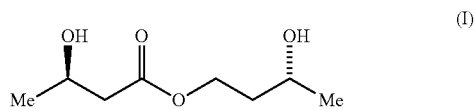 [SMILES: C[C@@H](O)CCOC(=O)C[C@@H](C)O]

The invention further provides an ingestible composition which comprises a compound of the invention as defined above and a dietetically or pharmaceutically acceptable carrier.

(3R)-Hydroxybutyl (3R)-hydroxybutyrate reduces plasma levels of fatty acids. The invention therefore further provides a compound of the invention as defined above for use in treating a condition which is caused by, exacerbated by or associated with elevated plasma levels of free fatty acids in a human or animal subject.

In one embodiment, the invention further provides a compound of the invention as defined above for use in treating a condition where weight loss or weight gain is implicated. Thus, the compound may be used to treat obesity or other overweight conditions, to promote weight loss, to maintain a healthy weight, or to decrease the ratio of fat to lean muscle in a subject (which may be a healthy subject or a compromised subject). The compound may be used as a dietary supplement.

The invention further provides a compound of the invention as defined above for use in promoting alertness or improving cognitive function, or in treating cognitive dysfunction.

The invention also provides a compound of the invention as defined above for use in treating, preventing, or reducing the effects of, neurodegeneration, free radical toxicity, hypoxic conditions or hyperglycaemia.

DETAILED DESCRIPTION OF THE INVENTION

Figure 1:
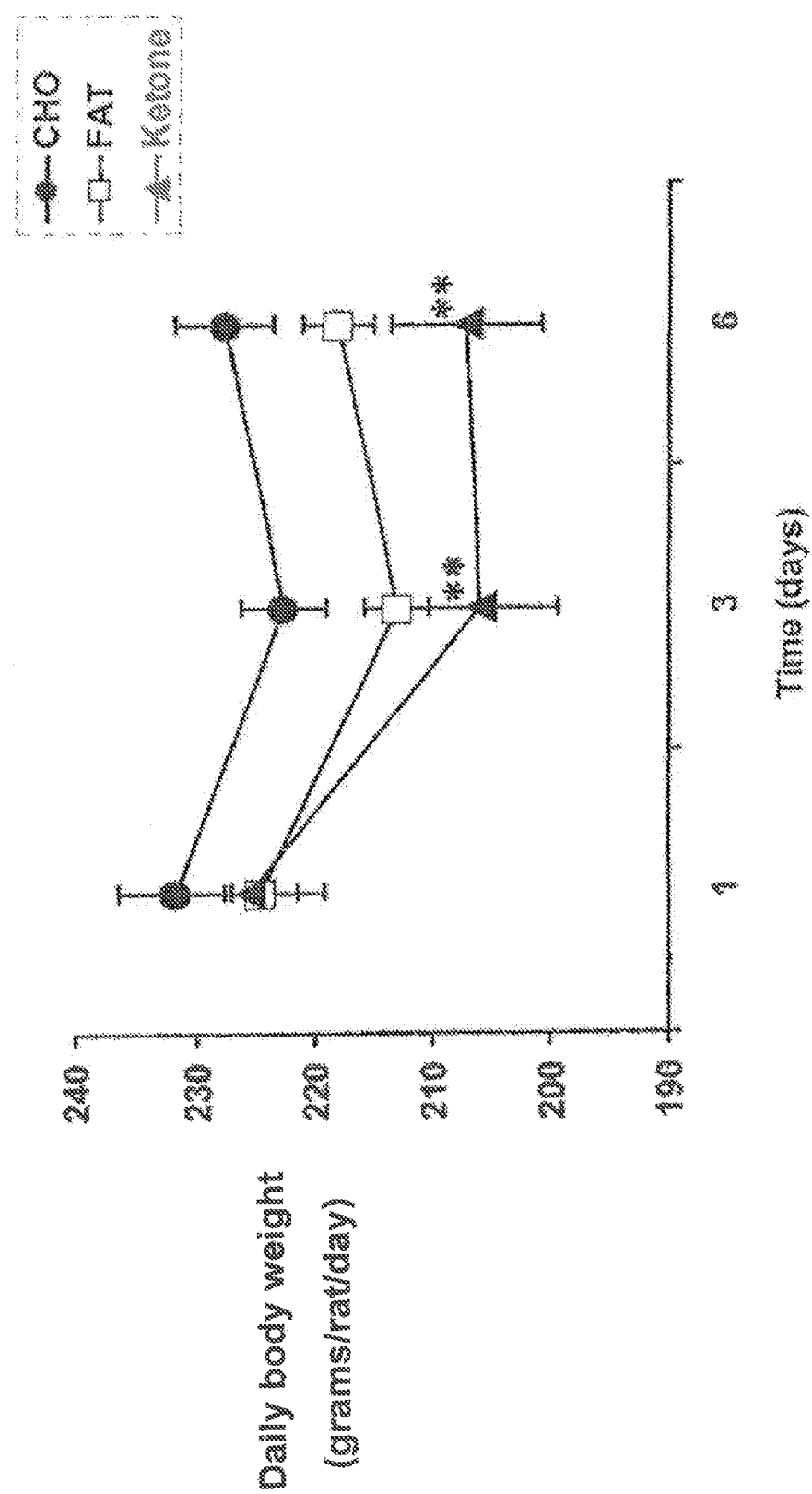
FIG. 1 shows a plot of daily body weight (in grams/rat/day) of rats fed a diet of carbohydrate, fat or the compound of the invention ("ketone"), in the test described in Example 3.

The compound of the invention is 3-hydroxybutyl 3-hydroxybutyrate enantiomerically enriched with respect to the (3R, 3R') enantiomer. The term "enriched" as employed herein means that the level of the enriching isomer is higher than the level at which that isomer would typically be produced in a racemic mixture.
Where a percentage enrichment is referred to, the enriching isomer constitutes that percentage of the total 3-hydroxybutyl 3-hydroxybutyrate present. Generally the 3-hydroxybutyl 3-hydroxybutyrate in the present invention is enantiomerically enriched to at least 90%, preferably 95% with respect to (3R)-hydroxybutyl (3R)-hydroxybutyrate. In other words, of the total 3-hydroxybutyl 3-hydroxybutyrate present, at least 90% and preferably 95% is the (3R)-hydroxybutyl (3R)-hydroxybutyrate isomer. In a further embodiment the 3-hydroxybutyl 3-hydroxybutyrate may comprise at least 97%, for example 98%, or 99%, of the (3R,3R') enantiomer.

The compound of the invention as defined above may be prepared by a process which comprises carrying out a transesterification reaction between ethyl (3R)-hydroxybutyrate and (3R)-1, 3-butanediol in the presence of a lipase enzyme. The reaction is typically conducted at about 40° C. for a period of about 96 hours. An example of the process is described in Example 1 which follows. The product of the reaction is typically submitted to wiped film distillation (GMP). This comprises a degassing pass, a second light cut pass to remove starting materials and then a final pass. The conditions of the final pass are typically 145° C. at 1.8 Ton.

A sample of 3-hydroxybutyl 3-hydroxybutyrate enriched with respect to the (3R, 3R') enantiomer gives measurably raised blood levels of (3R)-hydroxybutyrate, a ketone body, when ingested orally. The compound of the invention therefore represents an effective means of delivering (3R)-hydroxybutyrate to a subject.

Two particular advantages are associated with the invention. First, the (3R, 3R') enantiomer is palatable and is less bitter-tasting than other ketone bodies. It is therefore particularly well-suited for oral administration. This contrasts with many other ketone bodies, and their derivatives and precursors, which are notoriously bad-tasting and thus difficult to tolerate when taken orally. Second, the (3R, 3R') enantiomer is cleaved in vivo to form (3R)-hydroxybutyrate and (R)-1,3-butanediol. The (3R)-hydroxybutyrate is released immediately, giving a rapid effect following ingestion. The (R)-1,3-butanediol is converted in the liver to (3R)-hydroxybutyrate which is then released into blood. Overall this gives a favourable pharmacokinetic profile, since raised blood levels of the desired (R)-3-hydroxybutyrate are both achieved quickly and then sustained over a period of time following ingestion of the compound of the invention.

The compound of the invention as defined above reduces plasma levels of fatty acids. A compound of the invention may therefore be used to reduce the level of free fatty acids circulating in the plasma of a subject. As such it may be used to treat a condition which is caused by, exacerbated by or associated with elevated plasma levels of free fatty acids in a human or animal subject. A human or animal subject may therefore be treated by a method which comprises the administration thereto of a compound of the invention as defined above. The condition of the subject may thereby be improved or ameliorated.

Conditions which are caused by, exacerbated by or associated with elevated plasma levels of free fatty acids include, but are not limited to: neurodegenerative diseases or disorders, for instance Alzheimer's disease, Parkinson's disease, Huntington's chorea; hypoxic states, for instance angina pectoris, extreme physical exertion, intermittent claudication, hypoxia, stroke and myocardial infarction; insulin resistant states, for instance infection, stress, obesity, diabetes and heart failure; and inflammatory states including infection and autoimmune disease.

In addition to reducing plasma levels of fatty acids, a compound of the invention acts on the appetite centres in the brain. In particular, a compound of the invention increases the levels of various anorexigenic neuropeptides (neuropeptides known to be associated with decreased food intake and decreased appetite) in the appetite centres of the brain and also induces higher levels of malonyl CoA, a metabolite associated with decreased appetite and food intake. The invention therefore further provides a compound of the invention as defined above for use in treating a condition where weight loss or weight gain is implicated. For example, the compound may be used in suppressing appetite, treating obesity, promoting weight loss, maintaining a healthy weight or decreasing the ratio of fat to lean muscle in a subject. The subject in each case may be a healthy subject or a compromised subject. A healthy subject may be, for instance, an individual of healthy weight for whom physical performance and/or physical appearance is important. Examples include members of the military, athletes, body builders and fashion models. A compromised subject may be an individual of non-healthy weight, for instance an individual who is overweight, clinically obese or clinically very obese. A compromised subject may alternatively be an individual of healthy or non-healthy weight who is suffering from a clinical Condition, for instance a condition listed below.

An individual of healthy weight has a body mass index (BMI) of 18.5 to 24.9; an individual who is overweight has a body mass index (BMI) of from 25 to 29.9; an individual who is clinically obese has a body mass index of from 30 to 39.9; and an individual who is clinically very obese has a body mass index of 40 or more.

In addition to reducing plasma levels of fatty acids and acting on the appetite centre in the brain, a compound of the invention increases brain metabolic efficiency, by increasing brain phosphorylation potential and the $\Delta G'$ of ATP hydrolysis. A compound of the invention thereby promotes improved cognitive function and can be used to treat cognitive dysfunction or to reduce the effects of neurodegeneration. A compound of the invention also increases the level of the neuropeptide Brain Derived Neurotropic Factor (BDNF) in both the paraventricular nucleus (the appetite centre of the brain) and the hippocampus (a part of the brain known to be important for memory). As well as decreasing appetite, BDNF is known to prevent apoptosis and promote neuronal growth in basal ganglia and other areas of interest, thus the increased levels of BDNF produced by the compound of the invention are expected to inhibit neurodegeneration, limit neural tissue death after hypoxia or trauma and promote neural tissue growth.

A compound of the invention also increases the level of the anorexigenic neuropeptide Cocaine-and-Amphetamine Responsive Transcript (CART). CART is known to promote alertness as well as to decrease appetite. Thus, the increased levels of CART produced by the compound of the invention are expected to improve cognitive function.

The compounds of the invention are therefore useful for (a) promoting alertness and improved cognitive function, and (b) inhibiting neurodegeneration. The invention therefore further provides a compound of the invention as defined above for use in promoting alertness or improving cognitive function, or in treating cognitive dysfunction.

The invention also provides a compound of the invention as defined above for use in treating, preventing, or reducing the effects of, neurodegeneration, free radical toxicity, hypoxic conditions or hyperglycaemia.

In one embodiment, the compound of the invention as defined above is for use in treating, preventing, or reducing the effects of, neurodegeneration. A compound of the invention may be used to treat, prevent, or reduce the effects of neurodegeneration arising from any particular cause. The neurodegeneration may for instance be caused by a neurodegenerative disease or disorder, or may be caused by aging, trauma, anoxia and the like. Examples of neurodegenerative diseases or disorders that can be treated using a compound of the invention include, but are not limited to Alzheimer's disease, Parkinson's disease, amyotrophic lateral sclerosis, epilepsy, astrocytoma, glioblastoma and Huntington's chorea.

Further examples of conditions which a compound of the invention may be used to prevent or treat include muscle impairment, fatigue and muscle fatigue. Muscle impairment and muscle fatigue may be prevented or treated in a healthy or compromised subject. A compromised subject may be, for instance, an individual suffering from myalgic encephalopathy (ME, or chronic fatigue syndrome) or the symptoms thereof. A compound of the invention may also be used to treat a patient suffering from a condition such as diabetes, metabolic syndrome X or hyperthyroidism, or a geriatric patient.

The aforementioned conditions are further examples of conditions which are caused by, exacerbated by or associated with elevated plasma levels of free fatty acids; the monoester compound of the invention can therefore be used to treat these conditions.

In another embodiment, a compound of the invention is used to treat a patient suffering from a condition selected from diabetes, hyperpyrexia, hyperthyroidism, metabolic syndrome X, fever and infection, or a geriatric patient.

A compound of the invention may be administered in combination with one or more additional agents, for instance an agent selected from micronutrients and medicaments. The compound of the invention and the additional agent may be formulated together in a single composition for ingestion. Alternatively the compound of the invention and the additional agent may be formulated separately for separate, simultaneous or sequential administration.

When the additional agent is a medicament it may be, for instance, a standard therapy for a condition from which the subject is suffering. For instance, a compound of the invention may be administered in combination with conventional anti-diabetic agents to a subject suffering from diabetes. Conventional anti-diabetic agents include insulin sensitisers such as the thiazolidinediones, insulin secretogogues such as sulphonylureas, biguanide antihyperglycemic agents such as metformin, and combinations thereof.

When the additional agent is a micronutrient it may be, for instance, a mineral or a vitamin. Examples include iron, calcium, magnesium, vitamin A, the B vitamins, vitamin C, vitamin D and vitamin E.

Ketone bodies act on niacin receptors. A compound of the invention may therefore advantageously be administered in combination with niacin (vitamin B3) as both ketone bodies and niacin act on adipose tissue to inhibit free fatty acid release.

The compound of the invention as defined above, namely 3-hydroxybutyl 3-hydroxybutyrate enantiomerically enriched with respect to the (3R, 3R') enantiomer, can be formulated into an ingestible composition which further comprises a dietetically or pharmaceutically acceptable carrier. The compositions may be food products, beverages, drinks, supplements, dietary supplements, functional foods, nutraceuticals or medicaments.

The concentration of the compound of the invention in the ingestible composition depends on a variety of factors, including the particular format of the composition, the intended use of the composition and the target population. Generally the composition will contain the compound of the invention in an amount effective to reduce plasma levels of free fatty acids. Typically the amount is that required to achieve a circulating concentration of beta-hydroxybutyrate (bHB) and/or acetoacetate of from 10 µM to 20 mM, preferably from 50 µM to 10 mM, more preferably from 100 µM to 5 mM, in a subject who ingests the composition. In one embodiment, an amount is used to achieve a circulating concentration of from 0.7 mM to 5 mM, for example from 1 mM to 5 mM.

The subject of the present invention is hydrolysed rapidly into two natural products, beta-hydroxybutyrate (bHB) and (R)-1,3-butanediol, and is therefore a natural calorie source which can be classified as a food and can form part of a food product.

A food product is an edible material composed primarily of one or more of the macronutrients protein, carbohydrate and fat, which is used in the body of an organism to sustain growth, repair damage, aid vital processes or furnish energy. A food product may also contain one or more micronutrients such as vitamins or minerals, or additional dietary ingredients such as flavourants and colourants.

Examples of food products into which the compound of the invention may be incorporated as an additive include snack bars, meal replacement bars, cereals, confectionery and probiotic formulations including yoghurts.

Examples of beverages and drinks include soft beverages, energy drinks, dry drink mixes, nutritional beverages, meal or food replacement drinks, compositions for rehydration (for instance during or after exercise) and herbal teas for infusion or herbal blends for decoction in water.

A composition for rehydration typically comprises water, a sugar carbohydrate and the compound of the invention. The composition may also comprise suitable flavourings, colourants and preservatives, as will be appreciated by the skilled person. The carbohydrate sugar is present as an energy source, and suitable sugars are known, including glucose and trehalose. A meal or food replacement drink may be of the type commonly advocated for use in weight loss regimens. Such drink formulations typically comprise appropriate quantities of one or more macronutrients, i.e. sources of protein, fat and/or carbohydrate, together with optional additional ingredients such as solubilising agents, preservatives, sweetening agents, flavouring agents and colourants.

A nutraceutical is a food ingredient, food supplement or food product which is considered to provide a medical or health benefit, including the prevention and treatment of disease. In general a nutraceutical is specifically adapted to confer a particular health benefit on the consumer. A nutraceutical typically comprises a micronutrient such as a vitamin, mineral, herb or phytochemical at a higher level than would be found in a corresponding regular food product. That level is typically selected to optimise the intended health benefit of the nutraceutical when taken either as a single serving or as part of a diet regimen or course of nutritional therapy. In the present case the level would be a level effective to reduce plasma levels of fatty acids, A functional food is a food that is marketed as providing a health benefit beyond that of supplying pure nutrition to the consumer. A functional food typically incorporates an ingredient such as a micronutrient as mentioned above, which confers a specific medical or physiological benefit other than a nutritional effect. A functional food typically carries a health claim on the packaging.

In accordance with the present invention a nutraceutical or functional food product typically contains the compound of the invention as defined above in an amount effective to lower plasma levels of free fatty acids in a subject. More typically the nutraceutical or functional food product contains the compound in an amount effective to suppress appetite, treat obesity or promote weight loss in a subject.

A dietary supplement is a product that is intended to supplement the normal diet of a human subject and which contains a dietary ingredient such as a vitamin, mineral, herb or other botanical product, or amino acid. A dietary supplement is typically presented in unit dosage format and is designed for consumption with, before or after food but not in place of food. A dietary supplement is thus often presented as a tablet or capsule, or as dried powder or granules for sprinkling over food or adding to water or a beverage.

A compound of the invention as defined above may be formulated into a medicament or a dietary supplement by mixing with a dietetically or pharmaceutically acceptable carrier or excipient. Such a earner or excipient may be a solvent, dispersion medium, coating, isotonic or absorption delaying agent, sweetener or the like. These include any and all solvents, dispersion media, coatings, isotonic and absorption delaying agents, sweeteners and the like. Suitable carriers may be prepared from a wide range of materials including, but not limited to, diluents, binders and adhesives, lubricants, disintegrants, colouring agents, bulking agents, flavouring agents, sweetening agents and miscellaneous materials such as buffers and adsorbents that may be needed in order to prepare a particular dosage form. The use of such media and agents for pharmaceutically active substances is well known in the art.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methyicellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methyicellulose, carboxymethylcellulose or polyvinyl alcohol.

A compound of the invention as defined above is also suitably formulated into granules or a powder. In this form it can be readily dispersed in water or other liquid such as tea or a soft drink for human subjects to drink, for instance a beverage or drink as described above. It may also be encapsulated, tabletted or formulated with a physiologically acceptable vehicle into unit dosage forms. A unit dosage can comprise a therapeutically effective amount of the extract for a single daily administration, or it can be formulated into smaller quantities to provide for multiple doses in a day. The composition may thus, for instance, be formulated into tablets, capsules, syrups, elixirs, enteral formulations or any other orally administrable form.

Examples of physiologically acceptable carriers include water, oil, emulsions, alcohol or any other suitable material.

The invention will be further described in the Examples which follow.

EXAMPLE 1

Synthesis of (3R)-hydroxybutyl (3R)-hydroxybutyrate

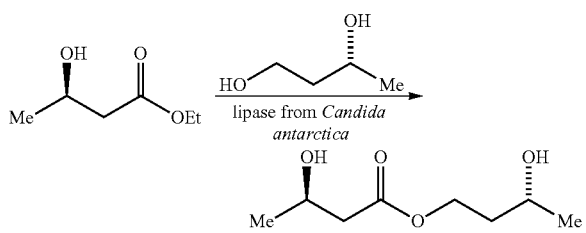

The ethyl (3R)-hydroxybutyrate (ca. 3 kg), (R)-1,3-butanediol (ca. 1.5 kg), and solid-supported *Candida antarctica* lipase B (ca. 300 g) are combined in a 20 liter rotary evaporator flask and placed on a large-scale Büchi evaporator. The system is evacuated to 8-10 torr with rotation at 40-45 C until the diol is consumed (as analysed by $^1$H NMR spectroscopy; ca. 3 days). The crude material is filtered (neat) to separate the enzyme and excess ethyl (3R)-hydroxybutyrate is removed by evaporation (to a final pressure and temperature of 2-3 torr and 80-85 C). Throughout, chilled water is circulated [−5 C during the reaction, +5 C during removal of ethyl (3R)-hydroxybutyrate]. Activated carbon (8 large spatula measures) is added, mixing on the rotary evaporator is continued for 15 min and then the neat mixture is filtered through a Celite® plug, the product (filtrate) being decanted directly into plastic vessels for storage. The Celite® plug is washed with ether (ca. 500 mL), the solvent removed from the washings in vacuo, and the residue added to the bulk for storage.

EXAMPLE 2

In vivo Testing of (3R)-hydroxybutyl (3R)-hydroxybutyrate-calorie-controlled Diets Young adult male Wistar rats (starting weight 70 g) (Harlan UK Limited) (n=50) were housed at approximately 20° C. on a 12h:12h reverse light:dark photoperiod. Rats were fed standard laboratory chow (Chow) (SDS, Essex, UK) prior to the starting the experimental diets: (a) normal "Western" diet (Western) in which 34% of kilocalories came from added palmitate (n=20), (b) high-carbohydrate (CHO) in which 70% of kilocalories came from added corn starch (n=10) or (c) (3R)-hydroxybutyl (3R)-hydroxybutyrate diet (monoester) in which 30% of kilocalories came from (3R)-hydroxybutyl (3R)-hydroxybutyrate (n=20).

The macronutrient compositions of the three diets are shown below. All diets contained the same energy in kCal/g but had different macronutrients.

TABLE 1

| Diet | Energy (kCal/g) | Fat | Protein | Carbohydrate (% kCal) | Monoester |
|---|---|---|---|---|---|
| Western | 1.76 | 34 | 27 | 39 | 0 |
| Carbohydrate | 1.76 | 4 | 26 | 70 | 0 |
| Monoester | 1.76 | 4 | 27 | 39 | 30 |

Diets and the monoester were manufactured at the University of Oxford. Water was provided ad libitum. This research project was approved by Oxford Animal Ethics Review Committees and the Home Office.

Rats were individually housed one week prior to the start of the experiments, so that they were accustomed to living in a solitary environment by the time the study started. They consumed standard laboratory chow ad libitum until they were placed on their experimental diet. Rats fed the Western and carbohydrate diets were fed the same number of calories as those consumed by the monoester-fed rats the previous day.

All rats were fed for 66 days. After this period the rat body, heart and fat pad weights were determined. The results are shown in Table 2:

TABLE 2

| Physical characteristic of rat | Western diet (n = 20) | Carbohydrate diet (n = 10) | Monoester diet (n = 20) |
|---|---|---|---|
| Final body weight (g) | 226 ± 5 | 213 ± 8 | 213 ± 5 |
| Heart weight (g) | 0.69 ± 0.02 | 0.65 ± 0.02 | 0.64 ± 0.02 |
| Heart to body weight (g) | 0.31 ± 0.01 | 0.31 ± 0.02 | 0.29 ± 0.01 |

TABLE 2-continued

| Physical characteristic of rat | Western diet (n = 20) | Carbohydrate diet (n = 10) | Monoester diet (n = 20) |
|---|---|---|---|
| Epididymal fat (g) | 2.49 ± 0.3 | 1.99 ± 0.2 | 1.48 ± 0.2* |
| Epididymal fat to body weight | 1.08 ± 0.2 | 0.93 ± 0.2 | 0.69 ± 0.1* |

*P < 0.05

The results in Table 2 show that the fat pad weight was significantly lower at the end of the 66-day test in the rats that had been fed the monoester diet than in the rats fed either the Western (i.e. high fat) diet or the carbohydrate diet. The fat to body weight was also significantly lower for the rats fed monoester.

EXAMPLE 3

In vivo Testing of (3R)-hydroxybutyl (3R)-hydroxybutyrate-meal-fed Diets

Example 2 was repeated using the same foods as shown in Table 1 but where the rats were meal-fed. Rats in this example therefore had a free choice of how much food to eat at each meal, rather than being calorifically-controlled as in Example 2.

The daily body weight (in grams per rat per day) was plotted against time for rats in each of the three diet groups over the first six days of the test. The resulting graph is shown in FIG. 1. One-way analysis of variance with Tukey-Kramer multiple comparison test was used (n=8 per group, **p<0.001). Significantly reduced body weight is seen from the $3^{rd}$ to $6^{th}$ days in rats fed the monoester diet. The body weight of rats in the group fed the carbohydrate diet remained high throughout the feeding process.

Figure 2:
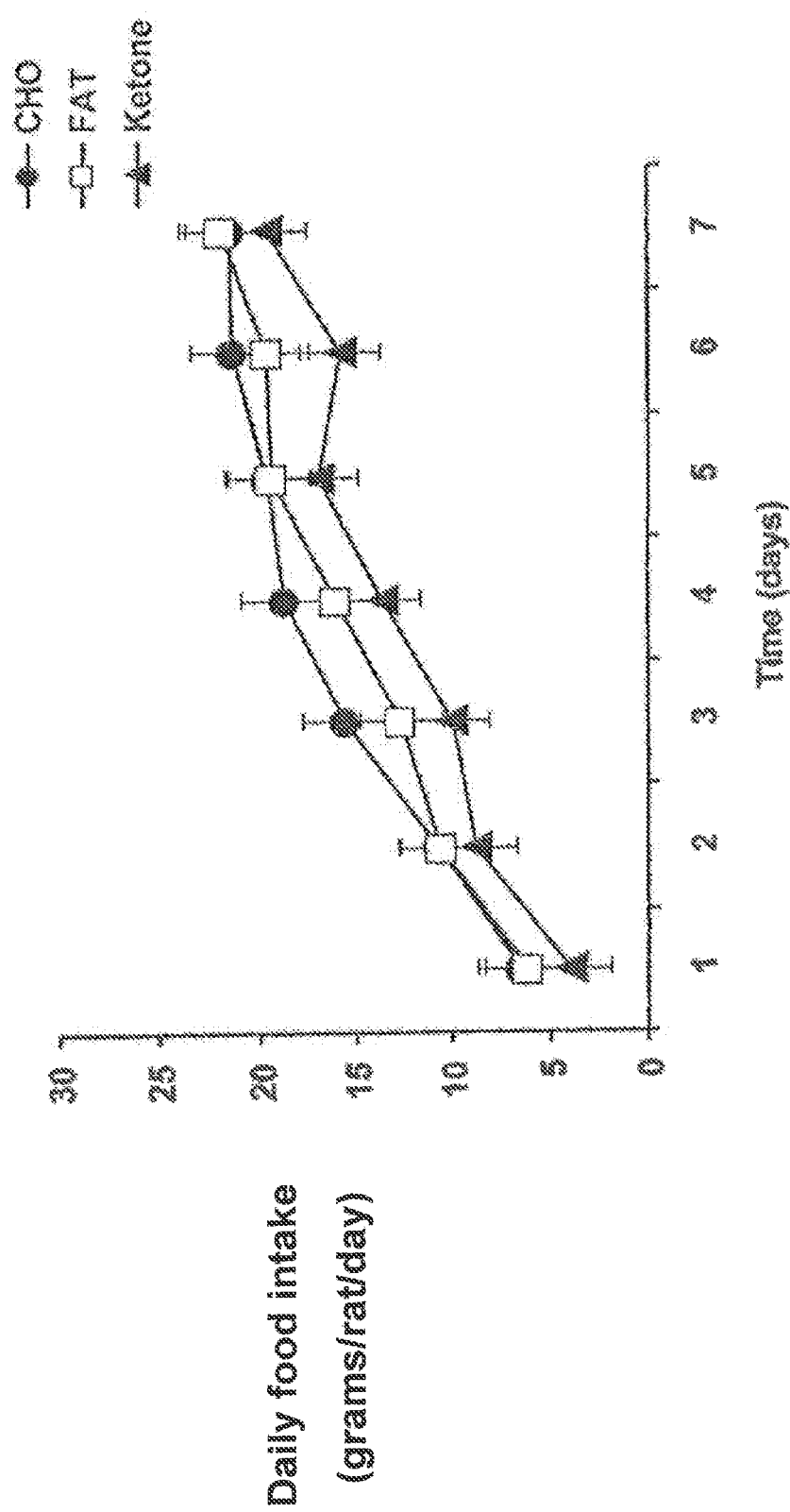
FIG. 2 shows a plot of daily food intake (in grams/rat/day) for rats fed a diet of carbohydrate, fat or the compound of the invention ("ketone"), in the test described in Example 3.

Meal-fed rats on the monoester diet ate less food and lost more weight than rats on the other two diets. The daily food intake (in grams per rat per day) was plotted against time for rats in each of the three diet groups over the first seven days of the test. The resulting graph is shown in FIG. 2. Again, one-way analysis of variance with Tukey-Kramer multiple comparison test was used (n=8 per group, ***p<0.001). Rats on the monoester diet displayed a consistently reduced daily food intake throughout the period compared with rats on the carbohydrate and Western diets.

EXAMPLE 4

In vivo Testing of (3R)-hydroxybutyl (3R)-hydroxybutyrate-isonitrogenous and Isocaloric Diets In a 28-day study, male and female Wistar rats weighing approximately 350 g were randomized to one of three diet groups (n=10 males and 10 females/group) and administered either a carbohydrate diet (CHOD), a normal human diet (NHD), or a ketone diet (KD). The diets were isonitrogenous and isocaloric, differing only in their relative amounts of carbohydrate, fat, and ketones. In the KD, the ketone used was the ketone monoester (3R)-hydroxybutyl (3R)-hydroxybutyrate diet (i.e. the compound of the invention). In the KD, approximately ⅓ of the energy was derived from the ketone ester, while in the NHD and CHOD, ⅓ of the energy was derived from palmitate and starch, respectively. The compositions of the experimental diets (expressed in terms of % of calories) are summarized in Table 3.

TABLE 3

|  | Ketone Diet (KD) | Normal Human Diet (NHD) | Carbohydrate Diet (CHOD) |
|---|---|---|---|
| Carbohydrate | 38.5 | 38.6 | 70.2 |
| Protein | 26.9 | 27.0 | 26.2 |
| Fat | 3.7 | 34.3 | 3.7 |
| Ketone monoester | 31 | 0 | 0 |
| Total | 100 | 100 | 100 |

The compositions of the experimental diets (g/100 g) are summarized in Table 4 below.

TABLE 4

|  | Ketone Diet | Normal Human Diet (NHD) | Carbohydrate Diet (CHOD) |
|---|---|---|---|
| Rodent chow | 25.7 | 25.7 | 25.7 |
| Sugar-free jelly | 13.4 | 13.4 | 13.4 |
| Water | 49.6 | 55.1 | 46.3 |
| Palm oil | 0 | 5.8 | 0 |
| Corn flour | 0 | 0 | 14.5 |
| Ketone monoester | 11.4 | 0 | 0 |
| Total | 100 | 100 | 100 |

On day 28 of the study, male rats in the KD group weighed significantly less than male rats in the CHOD and NHD groups (390±26 g vs. 418±15 g and 413±16 g, respectively). The total amount of weight gained by male rats in the KD group was significantly less than the total amount of weight gained by the CHOD and NHD groups. Feed consumption was significantly lower in males fed the KD compared with males fed the CHOD and NHD diets (feed intake during days 22 to 29: 239±17 g vs. 269±7 g and 269±7 g, respectively). The average intake of the ketone monoester in males was approximately 11 g/kg body weight/day.

On days 15, 22, and 28 of the study, female rats in the KD group weighed significantly less than female rats in the CHOD and NHD groups (on day 28: 240±13 g vs. 253±12 g and 258±13 g, respectively). The total amount of weight gained by female rats in the KD group was significantly less than the total amount of weight gained by the CHOD and NHD groups. Feed consumption was significantly lower in females fed the KD compared with females fed the CHOD and NHD diets (feed intake during days 22 to 29: 175±12 g vs. 191±5 g and 194±7 g, respectively). The average intake of the ketone monoester in females was approximately 13.0 g/kg body weight/day.

EXAMPLE 5

Effect of (3R)-hydroxybutyl (3R)-hydroxybutyrate on Neuropeptide Levels, Levels of Krebs Cycle and CoA Intermediates, and Levels of Free Nucleotides in the Brain In a 14-day study, Wistar rats weighing about 250 g were randomized to one of three diet groups (n=6 rats/group) and administered either a carbohydrate ("starch") diet, a normal human ("fat") diet or a ketone ester diet, in which the ketone ester used was the ketone monoester (3R)-hydroxybutyl (3R)-hydroxybutyrate diet (i.e. the compound of the invention). The three diets were eaten in pair fed meals for 3 hours per day. The composition of the diets expressed in terms of g/100 g are summarised in Table 5 and the compositions expressed in terms of % of calories are summarised in Table 6.

TABLE 5

| Component | Starch | Fat | Ketone Ester |
|---|---|---|---|
| Chow | 25.7 | 25.7 | 25.7 |
| Sugar Free Jello | 13.4 | 13.4 | 13.4 |
| Water | 46.3 | 55.1 | 49.6 |
| Palm Oil | 0 | 5.8 | 0 |
| Corn Starch | 14.5 | 0 | 0 |
| Ketone Ester | 0 | 0 | 11.4 |
| Total | 100 | 100 | 100 |

TABLE 6

| Component | Starch | Fat | Ketone Ester |
|---|---|---|---|
| Carbohydrate | 70.2 | 38.6 | 38.5 |
| Protein | 26.2 | 27 | 26.9 |
| Fat | 3.7 | 34.3 | 3.7 |
| Ketone Ester | 0 | 0 | 31 |
| Total | 100 | 100 | 100 |

The rats on the ketone ester diet were found to consume less food and gain less weight than those eating the diets supplemented by starch (carbohydrate) or fat. The results are consistent with the results in Examples 2 to 4.

After eating the 3 diets in pair fed meals for 3 hours per day for 14 days, the levels of various Krebs cycle and CoA intermediates in the brain were measured enzymatically and by mass spectrometry using standard techniques. The results are shown in Table 7.

As can be seen in Table 7, the ketone ester fed rats were found to have higher malonyl CoA levels in the brain (bold font in the table). Malonyl CoA is a metabolite known to be associated with decreased food intake; it is known to decrease appetite (Wolfgang, M. J. and Lane, M. D. (2006) *J. Biol. Chem.* 281, 37265-37269). These data are consistent with the use of a diet comprising the ketone compound of the invention to decrease appetite. The values in Table 7 are means, in µmoles/g wet weight, ±SEM with n=6 to 8. CoA's are given in nmol/g wet weight.

TABLE 7

BRAIN KREBS CYCLE AND COA INTERMEDIATES

|  | Starch | Fat | Ketone Ester |
|---|---|---|---|
| Citrate | 0.199 ± 0.006 | 0.205 ± 0.005 | 0.222 ± 0.010 |
| Isocitrate | 0.0080 ± 0.0006 | 0.0086 ± 0.0004 | 0.0093 ± 0.008 |
| α-keto-glutarate | 0.128 ± 0.007 | 0.138 ± 0.008 | 0.140 ± 0.008 |
| Succinyl CoA (µM) | 0.831 ± 0.075 | 0.777 ± 0.158 | 0.910 ± 0.207 |
| Succinate | 0.0800 ± 0.0022 | 0.0822 ± 0.0034 | 0.0864 ± 0.0033 |
| Fumarate | 0.0728 ± 0.0042 | 0.0801 ± 0.0055 | 0.0745 ± 0.0058 |
| L-Malate | 0.179 ± 0.011 | 0.192 ± 0.012 | 0.181 ± 0.013 |
| Calc Oxaloacetate | 0.0026 ± 0.0003 | 0.0021 ± 0.0001 | 0.0026 ± 0.0004 |
| Acetyl CoA (µM) | 7.87 ± 1.32 | 8.20 ± 1.02 | 6.43 ± 0.53 |
| Malonyl CoA (µM) | 0.954 ± 0.061 | 1.02 ± 0.14 | 1.26 ± 0.13 [a] |

[a] $p < 0.05$ between ketone ester and starch

After the rats were fed on the diets for 14 days, the ratios of free nucleotide and the free nucleotide concentrations were determined. Measurements were performed on the freeze blown brain and metabolite ratios of the rats calculated as previously described (Veech, R. L. et al, *J. Biol. Chem.* 254:

6538-47, 1979). The results are shown in Table 8. The values in Table 8 are given as means±SEM (n=6 to 8). Cytosolic pH was assumed to be 7.2.

TABLE 8

CALCULATED FREE NUCLEOTIDE RATIOS AND CALCULATED FREE NUCLEOTIDE CONCENTRATIONS

|  | Starch | Fat | Ketone Ester |
|---|---|---|---|
| Free [NAD$^+$]/[NADH] cytosol from Lactate/Pyruvate | 319 ± 23 | 256 ± 29 [a, b] | 357 ± 27 |
| Free [NAD$^+$]/[NADH] mitochochondria from αKGxNH$_4$$^+$/Glut | 0.62 ± 0.08 | 0.66 ± 0.06 | 0.80 ± 0.17 |
| Free [NAD$^+$]/[NADPH] cytosol from αKGxCO$_2$/IsoCit | 0.028 ± 0.002 | 0.028 ± 0.002 | 0.026 ± 0.003 |
| E$_h$CoQ/CoQH$_2$ mV from Fum/Succ | 29.6 ± 0.5 | 30.5 ± 0.8 | 28.9 ± 0.6 |
| Free [Mg$^{2+}$] mM from [Cit]/[Isocit] | 1.5 ± 0.26 | 1.5 ± 0.11 | 1.5 ± 0.13 |
| Phosphorylation Potential from Kg + g (Eqn 1) M$^{-1}$ | 27,100 ± 4,020 | 26,800 ± 2,700 | 38,100 ± 3,390 [a, b] |
| ΔG' ATP kJ/mol | −58.6 ± 0.4 | −58.6 ± 0.2 | −59.6 ± 0.2 [a, b] |
| Free [ADP] cytosol μM/g from PCr/Cr | 0.027 ± 0.001 | 0.027 ± 0.001 | 0.027 ± 0.001 |
| Free [AMP] cytosol μM/g from K$_{myokinase}$ | 0.0004 ± 0.00003 | 0.0004 ± 0.00003 | 0.0004 ± 0.00003 |

[a] p < 0.05 between ketone ester and starch,
[b] p < 0.05 between ketone ester and fat, both as judged by Mann-Whitney U test.

The results of Table show 8 that, after 14 days of diet, brain phosphorylation potential and ΔG' of ATP hydrolysis were significantly higher in the ketone ester fed rats than in the rats fed with the carbohydrate and fat diets. The only change in the brain of the ketone-fed rats was increased energy: phosphorylation and ΔG. This increased energy is consistent with the effects of ketones in the perfused working rat heart (Sato, K., Kashiwaya, Y., Keon, C. A., Tsuchiya, N., King, M. T., Radda, G. K., Chance, B., Clarke, K., and Veech, R. L. (1995) FASEB J. 9, 651-658). The huge redox changes that are observed in the heart with ketone perfusion are however not observed.

These data are consistent with the use of a diet comprising the ketone compound of the invention to increase brain metabolic efficiency and thereby promote improved cognitive function, treat or reduce the effects of neurodegenerative diseases such as Alzheimer's disease, Parkinson's disease and Huntington's chorea or, for instance, protect the brain and central nervous system against neurodegeneration due to aging, trauma, anoxia and the like.

Effects of the Ketone Compound of the Invention on Neuropeptide Signalling in the Brain After 14 days of feeding with the fat, carbohydrate or ketone ester diet, the levels of various neuropeptides known to be associated with decreased food intake and decreased appetite ("anorexigenic" peptides) were surveyed in the paraventricular nucleus (PVN) area of the hypothalamus and in the hippocampus of the rat brain. The neuropeptide levels were measured using standard antibody techniques performed on sectioned brains of the rats. The results are shown in the micrographs of FIGS. 3 to 9.

The peptides measured were Brain Derived Neurotropic Factor (BDNF), melanocyte-stimulating hormone receptor 4 (MC4R), and Cocaine-and-Amphetamine Responsive Transcript (CART). As well as being anorexigenic these peptides have other important actions, thus:

BDNF decreases appetite and is also known to prevent apoptosis in basal ganglia and other areas of interest, thus increased levels of BDNF are expected to inhibit neurodegeneration as well as decrease appetite;
CART is known to promote alertness and decrease appetite, in a manner similar to caffeine or modafinil (a mood-brightening and memory-enhancing stimulant drug), thus increased levels of CART are expected to improve cognitive function as well as decrease appetite;
MC4R facilitates the break down of a large peptide into various hormones including Melanocyte stimulating hormone, which in turn regulates appetite. Mutations in MC4R are known to cause obesity.

These peptides are therefore of central importance in many of the important therapeutic aspects of ketone ester feeding in addition to the suppression of appetite. Most particularly in a) the promotion of alterness and improved cognitive function, and b) the inhibition of neurodegeneration from variety of causes such as aging, trauma, anoxia and the like.

Figure 3:
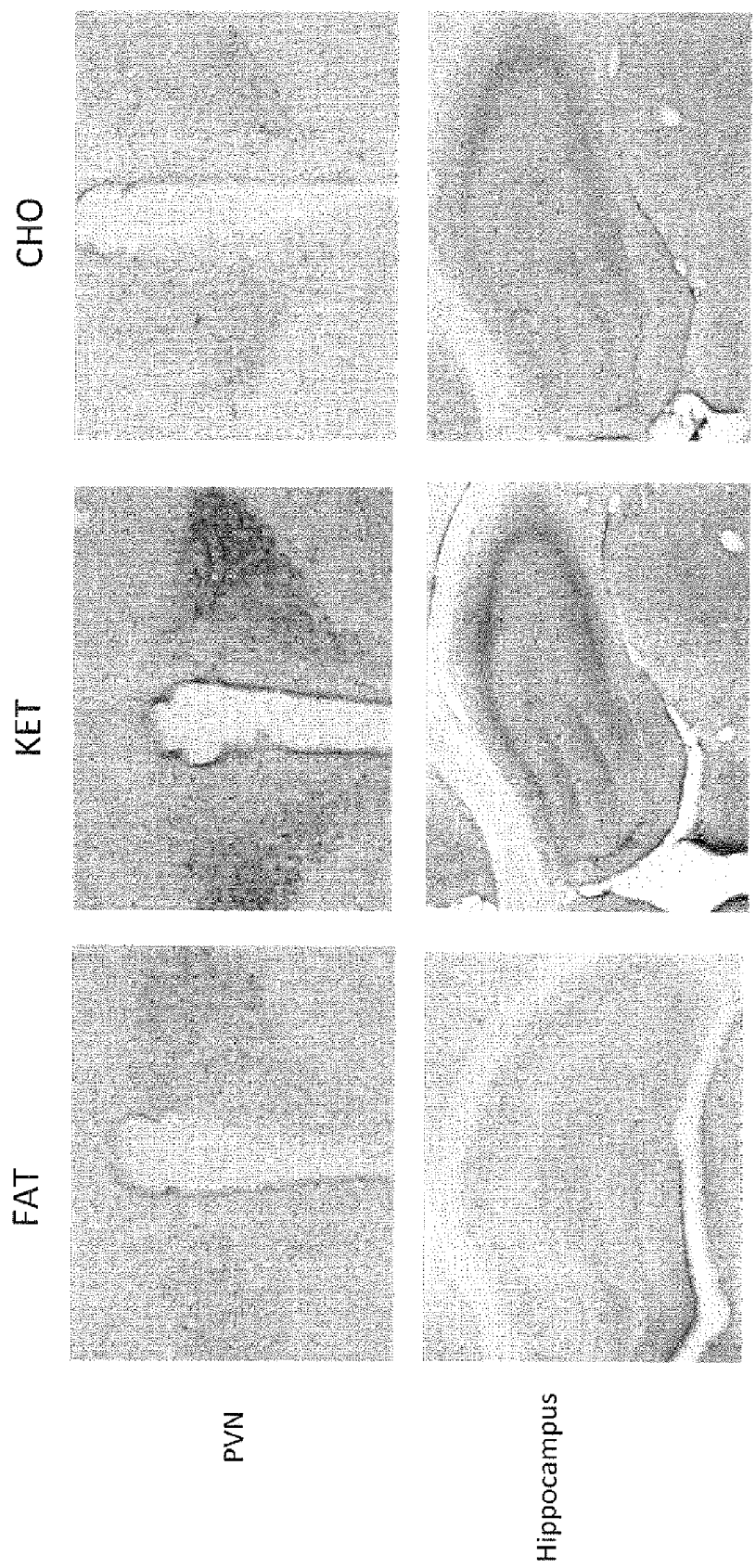
FIG. 3 contains micrographs showing the levels of BDNF positive cell bodies in the paraventricular nucleus (PVN) area of the hypothalamus and in the Hippocampus of rats treated for 4 days with a diet of fat, carbohydrate or the compound of the invention ("ketone"), in the test described in Example 5. A significantly greater number of BDNF-positive cell bodies is seen in the PVN of the rat treated with the ketone diet compared to fat and carbohydrate diet-treated rats. A similar observation is made in the hippocampus of rats treated with ketones.

The results in FIG. 3 show significantly more BDNF-positive cell bodies in the PVN of the rats treated with the ketone diet compared to fat and carbohydrate diet-treated rats. A similar observation is made in the hippocampus of rats treated with ketones. The PVN is a part of the brain which is known to control appetite, whereas the hippocampus is known to be important for memory. The results therefore support that a diet comprising the ketone compound of the invention can be used to decrease appetite, inhibit neurodegeneration and promote improved cognitive function.

Figure 4:
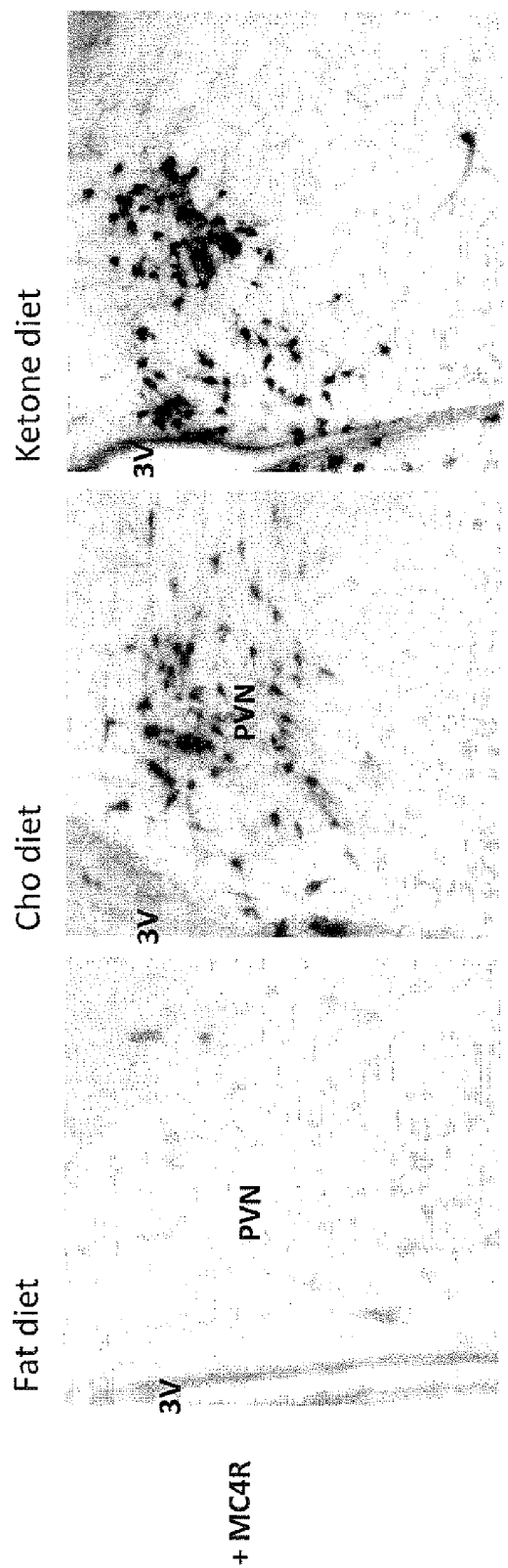
FIG. 4 presents micrographs showing the levels of MC4R positive cell bodies in the paraventricular nucleus (PVN) area of the hypothalamus of rats treated for 14 days with a diet of fat, carbohydrate or the compound of the invention ("ketone"), in the test described in Example 5. Significantly greater numbers of MC4R positive cell bodies are seen in the posterior magnocellular (pm) and medial parvocellular (mpd) regions of the PVN in rats treated with the ketone diet and the carbohydrate diet, than in rats treated with the fat diet.
Figure 5:
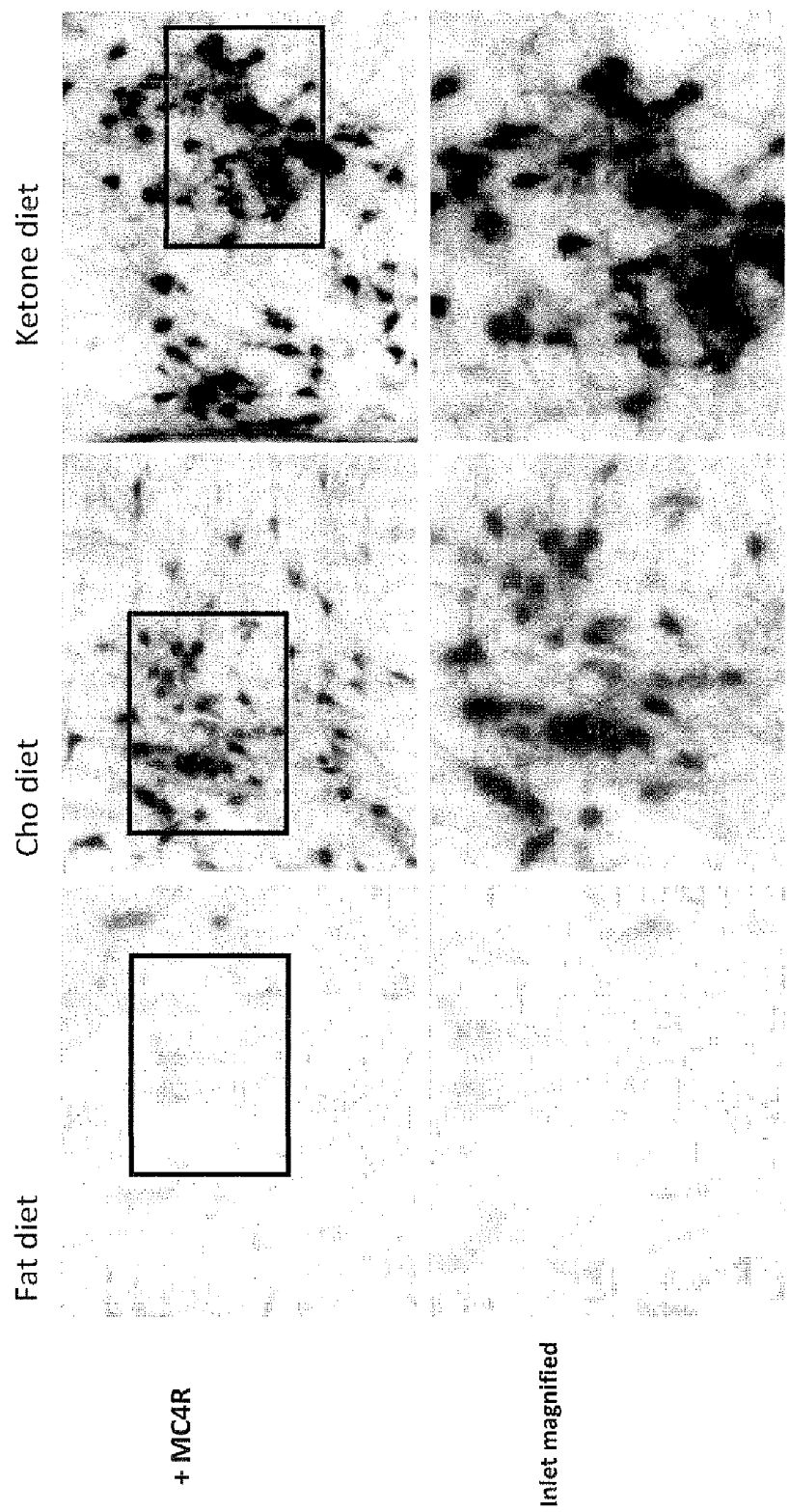
FIG. 5 shows magnifications of the micrographs in FIG. 5. The micrographs show the presence of a significantly denser area of MC4R positive cell bodies in the PVN of rats on the ketone diet or carbohydrate (Cho) diet compared to rats on the fat diet.

The micrographs in FIGS. 4 and 5 show a significantly higher density of MC4R positive cell bodies in the posterior magnocellular (pm) and medial parvocellular (mpd) regions of the PVN in rats treated with the ketone or carbohydrate (Cho) diet, compared to rats treated with the fat diet. This supports that a diet comprising the ketone compound of the invention can be used to decrease appetite and promote weight loss.

Figure 6:
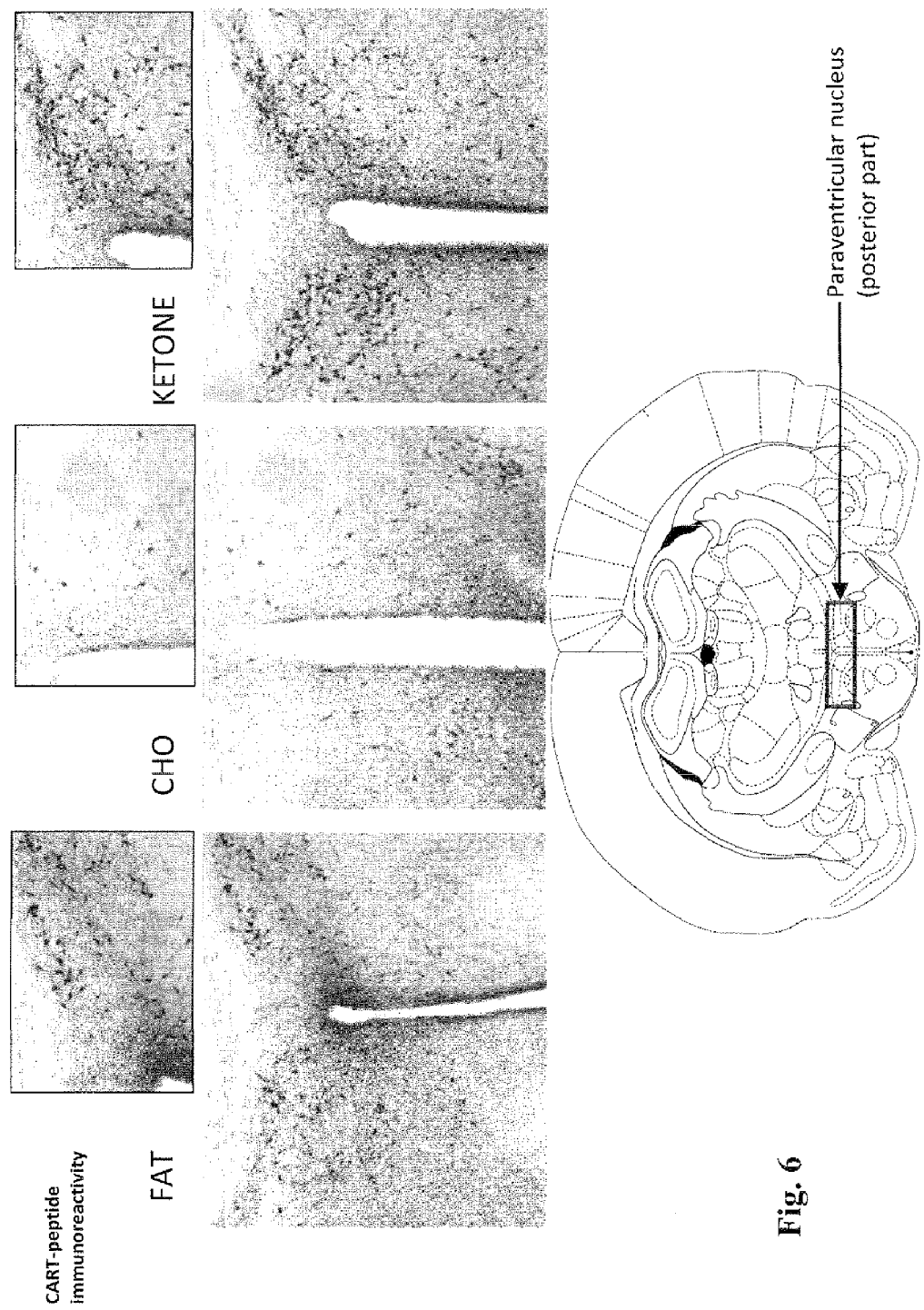
FIG. 6 contains micrographs showing the levels of CART in the posterior paraventricular nucleus (PVN) area of the hypothalamus of rats, treated for 14 days with a diet of fat, carbohydrate or the compound of the invention ("ketone"), in the test described in Example 5. Significantly greater numbers of CART positive cell bodies are seen in the PVNs of rats treated with the ketone and carbohydrate diets, than in the rats treated with the fat diet. The highest level of CART is seen in the PVN in the rats treated with the ketone diet.
Figure 7:
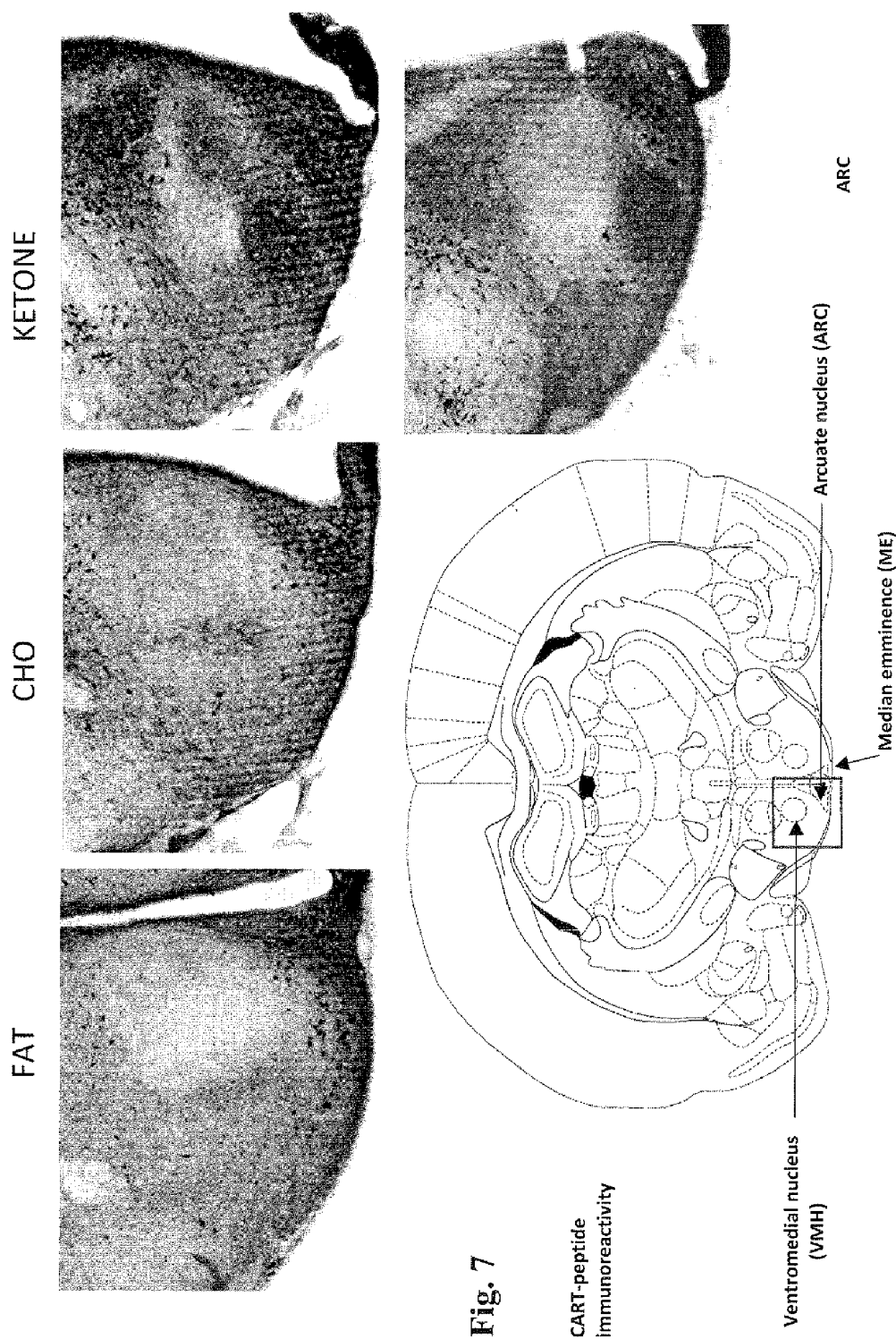
FIG. 7 presents micrographs showing the levels of CART in the ventromedial nucleus (VMH), arcuate nucleus (ARC) and median emminence (ME) areas of the hypothalamus of rats, treated for 14 days with a diet of fat, carbohydrate or the compound of the invention ("ketone"), in the test described in Example 5. The highest numbers of CART-positive cell bodies in these areas are seen in the rats treated with the ketone diet.
Figure 8:
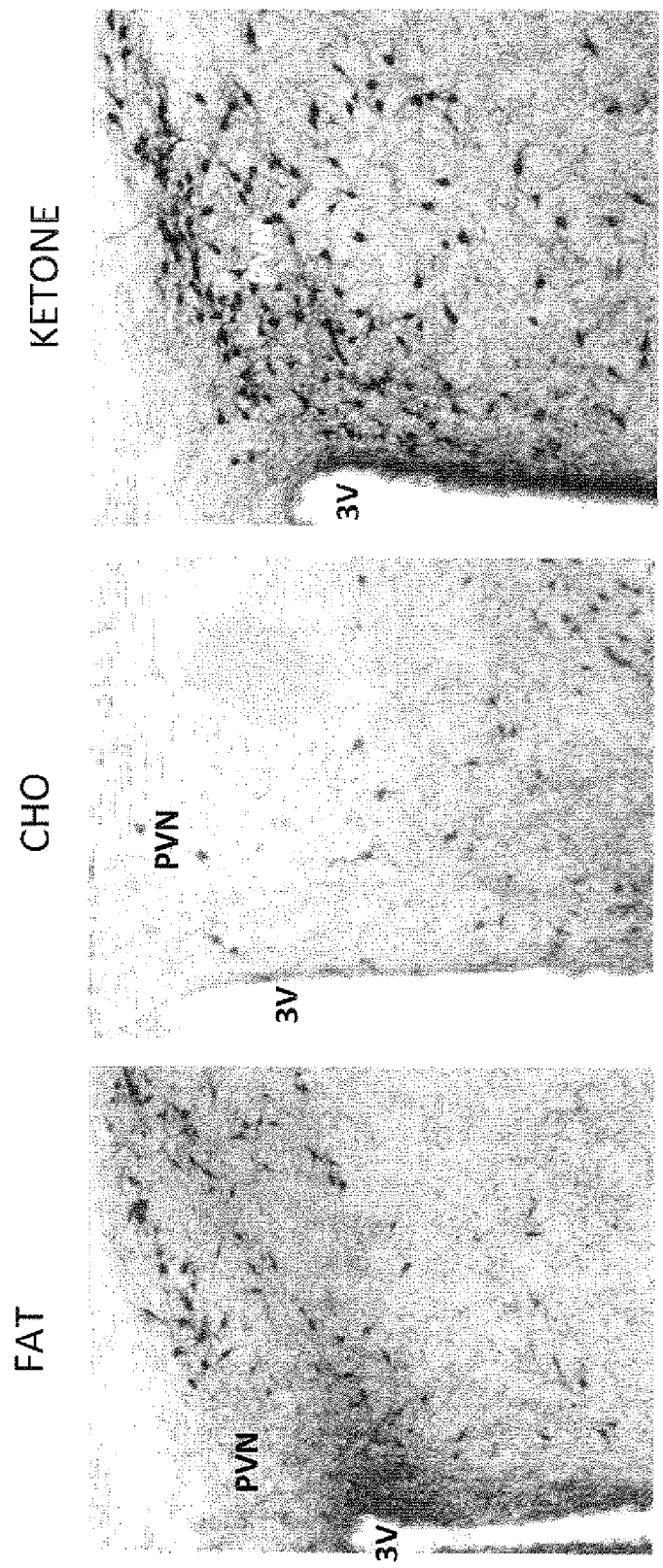
FIG. 8 shows a magnification of each of the micrographs in FIG. 7. The magnifications clearly show the presence of a significantly greater number of CART positive cell bodies in the PVN of rats on the ketone diet compared to rats on the fat and carbohydrate diets.
Figure 9:
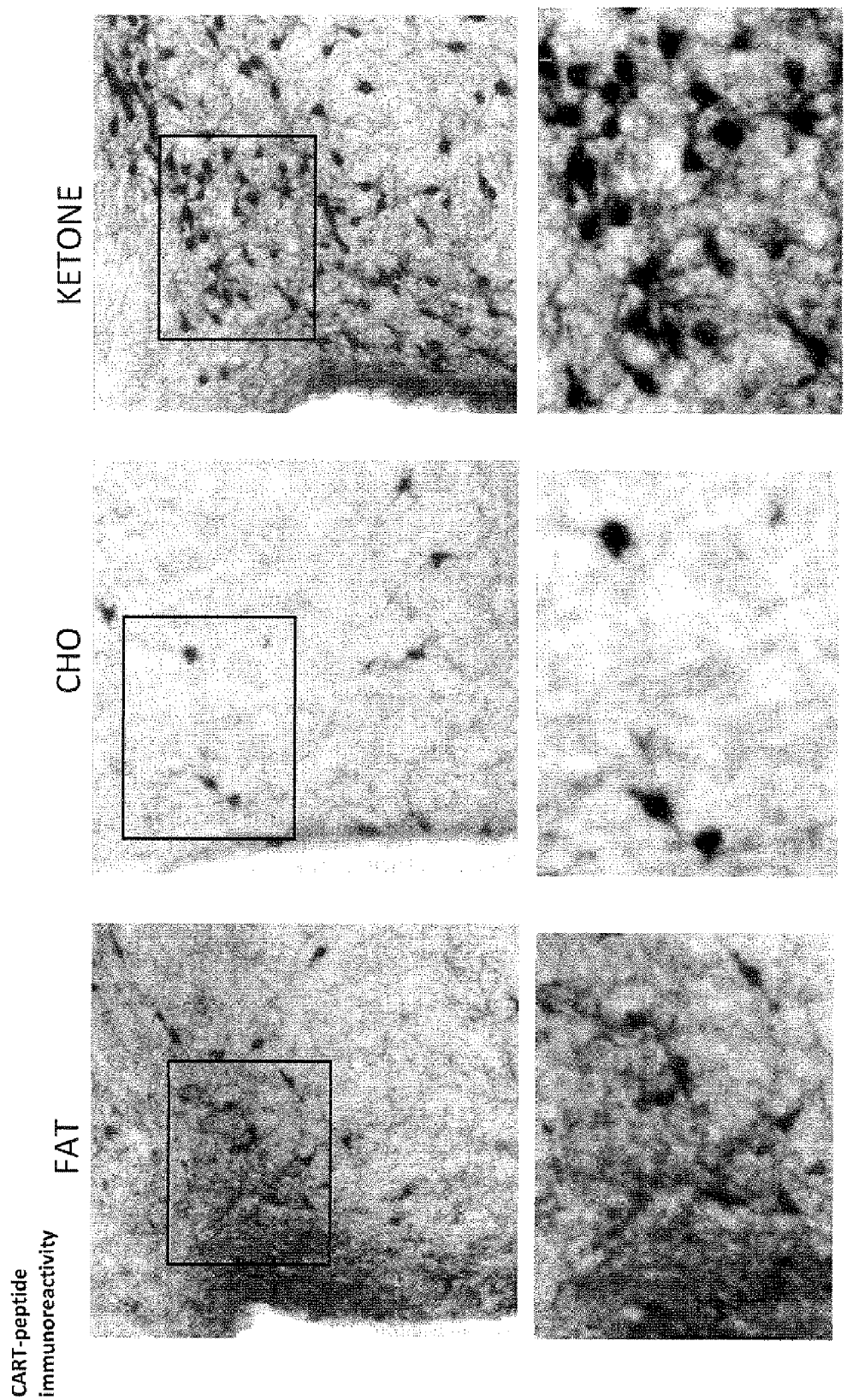
FIG. 9 shows further magnifications of the micrographs in FIGS. 7 and 9, showing that the PVN of the rats treated with the ketone diet has the highest density of CART-positive cell bodies.

FIGS. 6, 8 and 9 show the levels of CART in the posterior paraventricular nucleus (PVN) area of the hypothalamus of rats, treated for 14 days with the fat diet, carbohydrate diet or the diet comprising the ketone compound of the invention. FIG. 7 shows the levels of CART in the ventromedial nucleus (VMH), arcuate nucleus (ARC) and median emminence (ME) areas of the hypothalamus. Significantly greater numbers of CART positive cell bodies are seen in the PVNs of rats treated with the ketone and carbohydrate diets, than in the rats treated with the fat diet. The highest level of CART is seen in the PVN in the rats treated with the ketone diet. Furthermore, the rats treated with the ketone diet contain the highest number of CART-positive cell bodies in the ventromedial nucleus (VMH), arcuate nucleus (ARC) and median emminence (ME) areas of the hypothalamus. These results further support that a diet comprising the ketone compound of the invention can be used to decrease appetite, inhibit neurodegeneration and promote improved cognitive function. In summary, the micrographs in FIGS. 3 to 9 show that the ketone diet produces more BDNF in the paraventricular nucleus and hippocampus (FIG. 3);

more CART in the paraventricular nucleus (FIGS. 6 to 9); and more MC4R activity in the paraventricular nucleus (FIGS. 4 and 5).

These data are consistent with the use of a diet comprising the ketone compound of the invention to decrease appetite, inhibit neurodegeneration and promote improved cognitive function.

EXAMPLE 6

Tablet Composition

Tablets, each weighing 0.15 g and containing 25 mg of a compound of the invention were manufactured as follows:
Composition for 10,000 Tablets
Compound of the invention (250 g)
Lactose (800 g)
Corn starch (415 g)
Talc powder (30 g)
Magnesium stearate (5 g)

The compound of the invention, lactose and half of the corn starch were mixed. The mixture was then forced through a sieve 0.5 mm mesh size. Corn starch (10 g) is suspended in warm water (90 ml). The resulting paste was used to granulate the powder. The granulate was dried and broken up into small fragments on a sieve of 1.4 mm mesh size. The remaining quantity of starch, talc and magnesium was added, carefully mixed and processed into tablets.

EXAMPLE 7

Syrup Formulation

| | |
|---|---|
| Compound of invention | 250 mg |
| Sorbitol Solution | 1.50 g |

-continued

| | |
|---|---|
| Glycerol | 2.00 g |
| Sodium benzoate | 0.005 g |
| Flavour | 0.0125 ml |
| Purified Water q.s. to | 5.00 ml |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

We claim:

1. An ingestible composition comprising a compound which is 3-hydroxybutyl 3-hydroxybutyrate enantiomerically enriched with respect to (3R)-hydroxybutyl (3R)-hydroxybutyrate of formula (I):

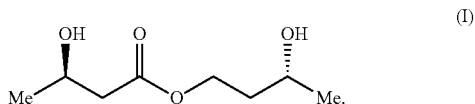 [SMILES: C[C@@H](O)CCOC(=O)C[C@@H](C)O]

and a dietetically or pharmaceutically acceptable carrier.

2. A composition according to claim 1 which is a food product, a beverage, a drink, a food supplement, a dietary supplement, a functional food, a nutraceutical or a medicament.

3. A method of treating a condition which is caused by, exacerbated by or associated with elevated plasma levels of free fatty acids in a human or animal subject, which method comprises administering to the subject a composition as defined in claim 1.

4. A method of suppressing appetite, treating obesity, promoting weight loss, maintaining a healthy weight or decreasing the ratio of fat to lean muscle, which method comprises administering to a subject in need thereof a composition as defined in claim 1.

5. A method of treating a condition selected from muscle impairment and muscle fatigue, which method comprises administering to a subject in need thereof a composition as defined in claim 1.

* * * * *